United States Patent [19]

Cerutti et al.

[11] Patent Number: 5,583,023

[45] Date of Patent: Dec. 10, 1996

[54] MODIFIED BACULOVIRUS, ITS PREPARATION PROCESS AND ITS APPLICATION AS A GENE EXPRESSION VECTOR

[75] Inventors: Martine Cerutti; Guy Croizier; Liliane Croizier; Gérard Devauchelle, all of St. Christopher, France

[73] Assignee: Institut National de la Recherche Agronomique, Paris, France

[21] Appl. No.: 355,824

[22] Filed: Dec. 14, 1994

Related U.S. Application Data

[63] Continuation of Ser. No. 908,188, Jul. 1, 1992, abandoned, which is a continuation of Ser. No. 358,799, May 30, 1989, abandoned.

[30] Foreign Application Priority Data

May 31, 1988 [FR] France .................................. 88 07207

[51] Int. Cl.⁶ ........................... C12N 15/66; C12N 15/64
[52] U.S. Cl. .................................... 435/172.3; 435/172.1; 435/320.1
[58] Field of Search .................. 435/69.1, 172.1, 435/172.3, 320.1; 536/24.1, 24.2

[56] References Cited

PUBLICATIONS

Muller et al. "Genetic Engineering", vol. 8. Eds, J. K. Setlow and A. Hollaender An Insect Baculovirus Host–Vector System for High Level Expression of Foreign genes, pp. 277–298.

*Primary Examiner*—David Guzo
*Attorney, Agent, or Firm*—Walter H. Dreger

[57] ABSTRACT

The present invention describes modified baculoviruses possessing unique restriction endonuclease cleavage sites downstream of the promoter of the baculovirus viral inclusion, polyhedron and/or protein P10 genes and a method for obtaining such modified baculoviruses. Such modified baculoviruses are useful for the direct cloning of heterologous DNA into the unique endonuclease restriction sites and the consequent expression of the heterologous DNA inserted therein.

5 Claims, 8 Drawing Sheets

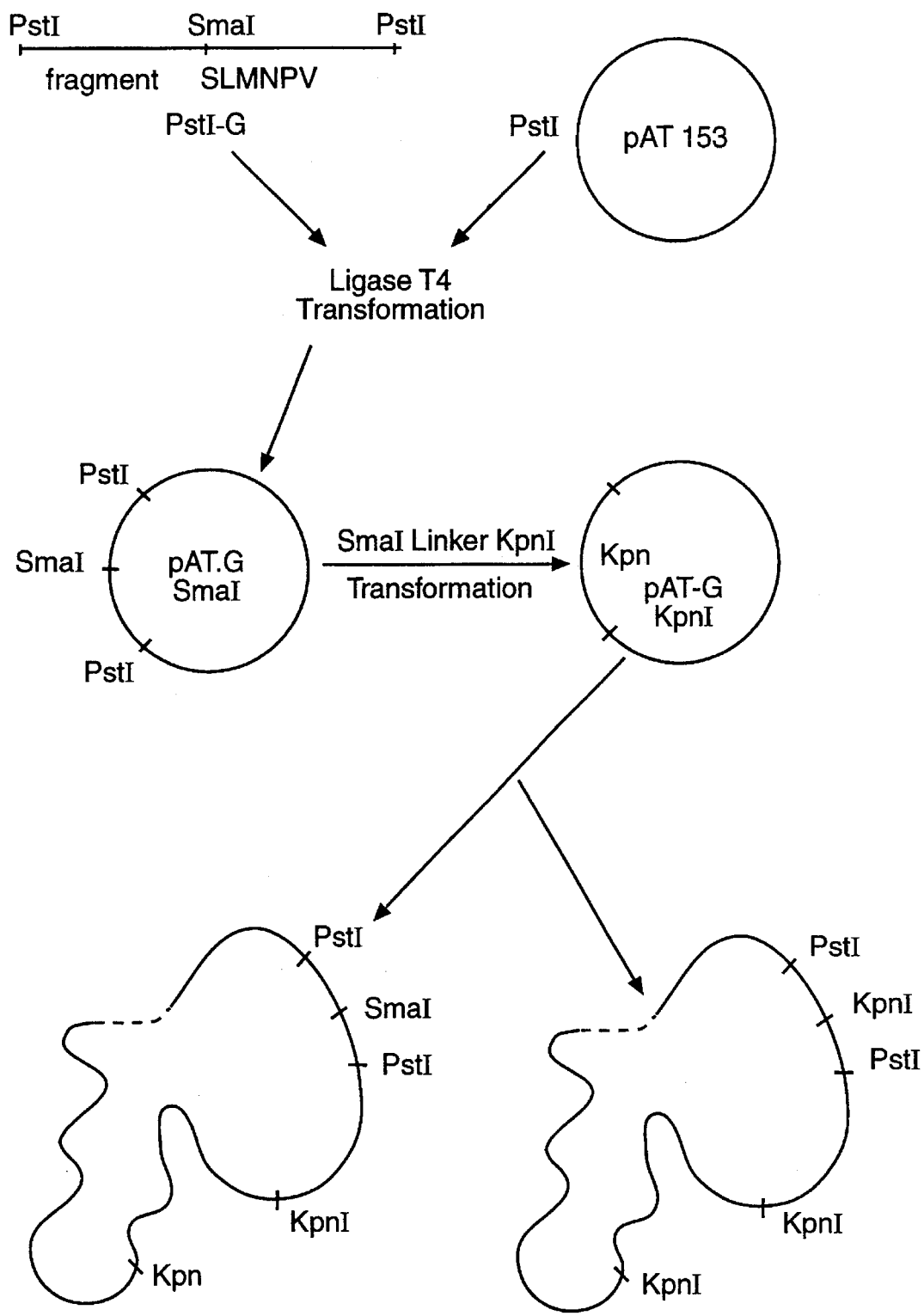
FIG._1

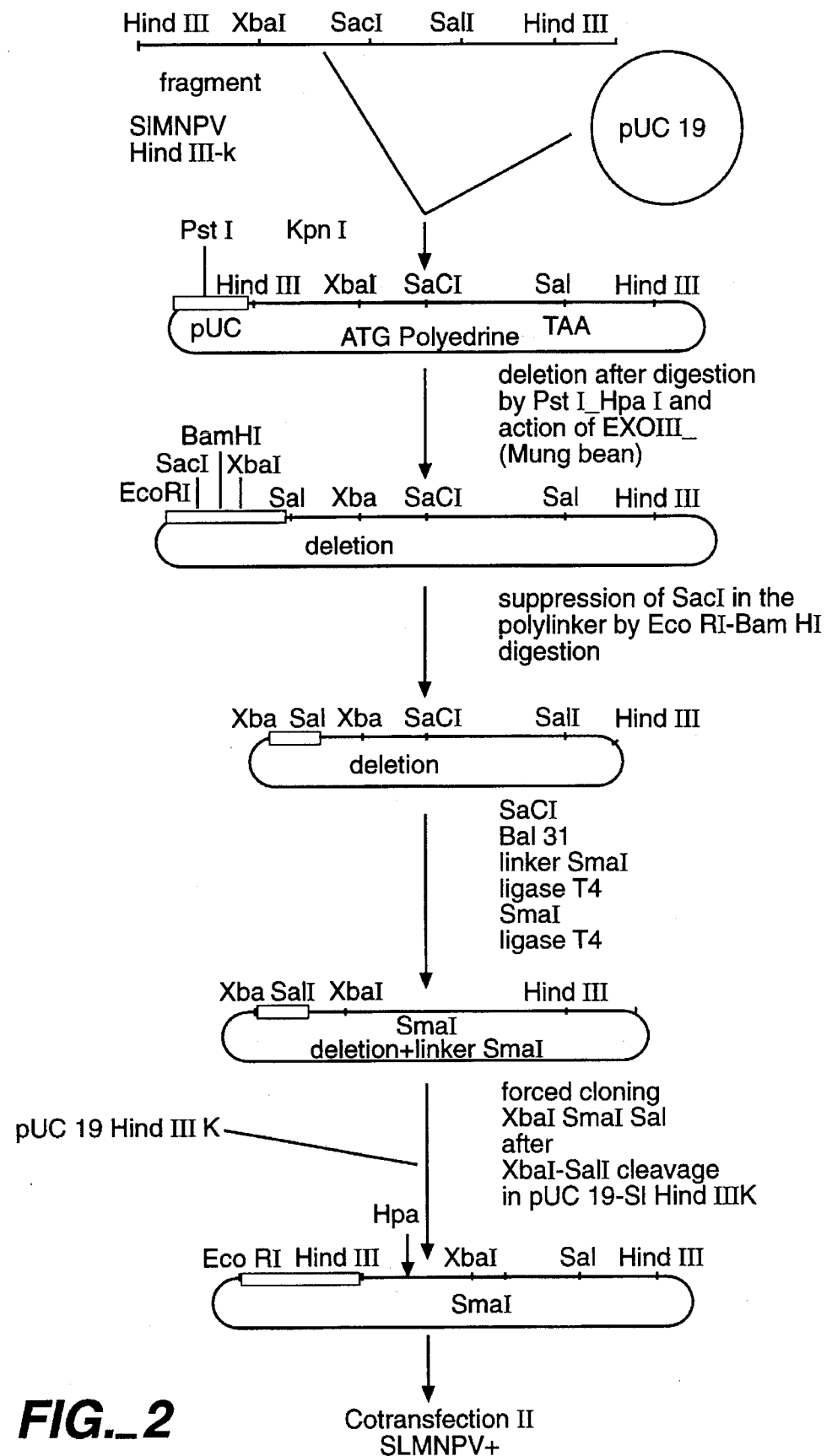
FIG._2

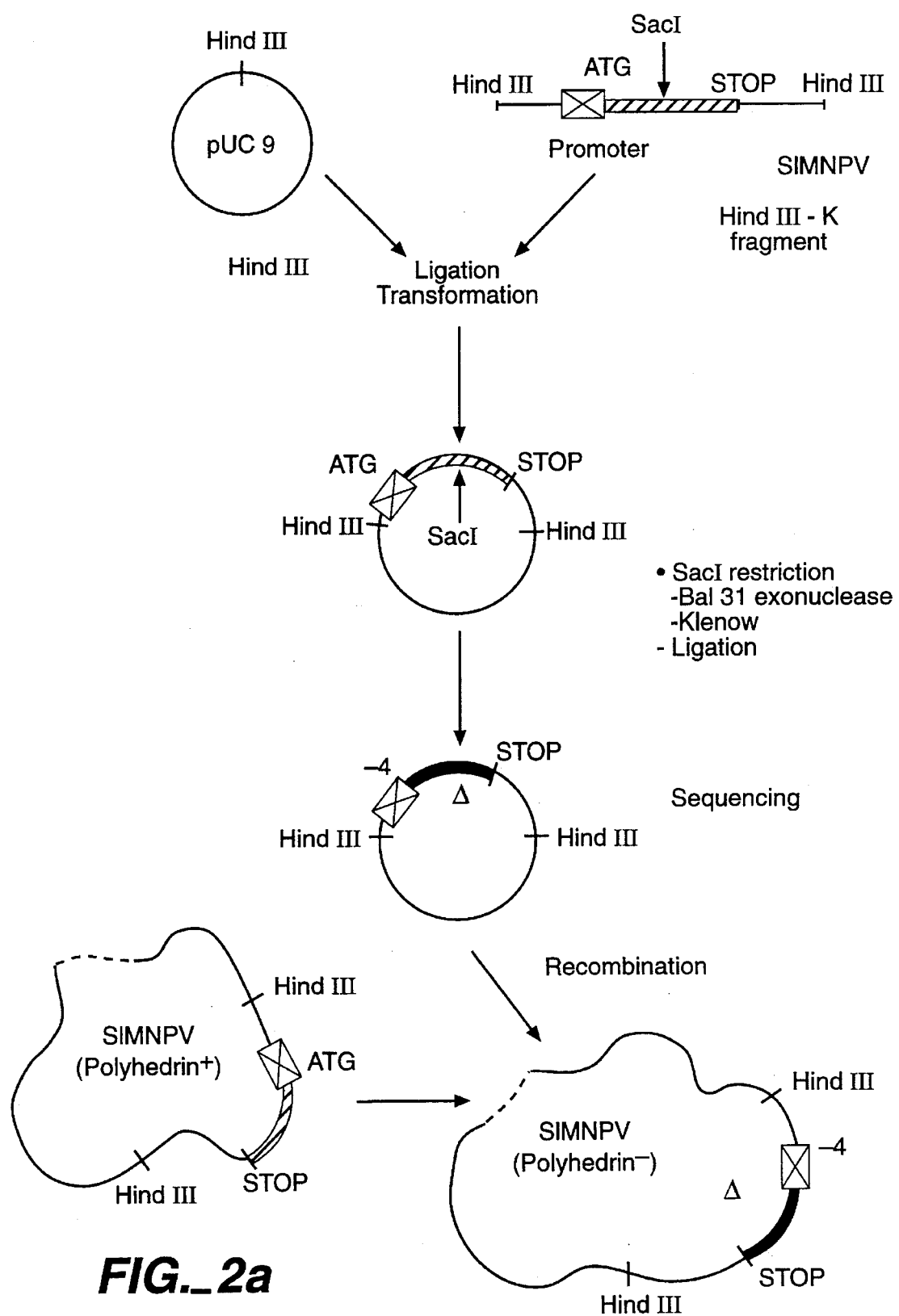
FIG._2a

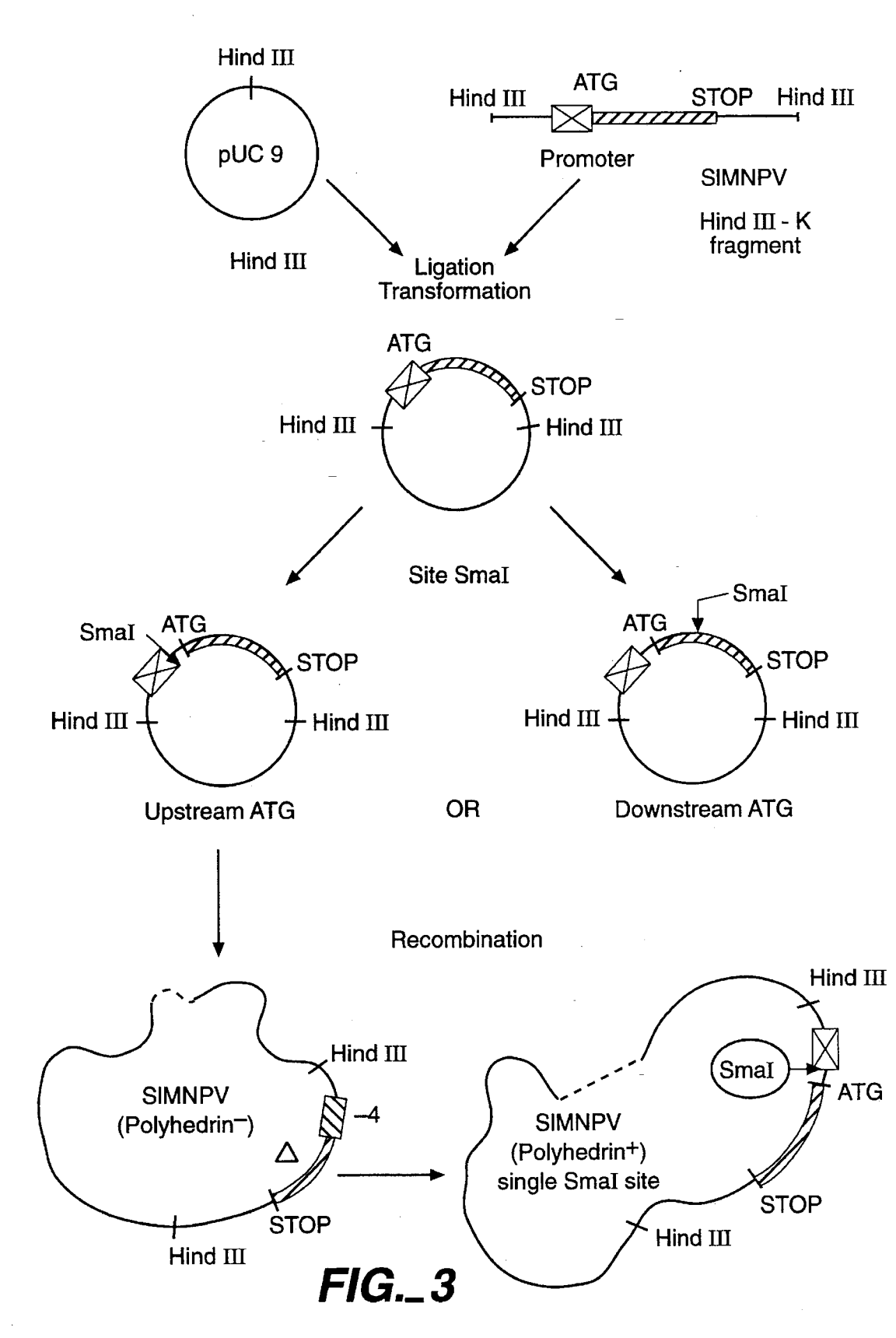

FIG._3

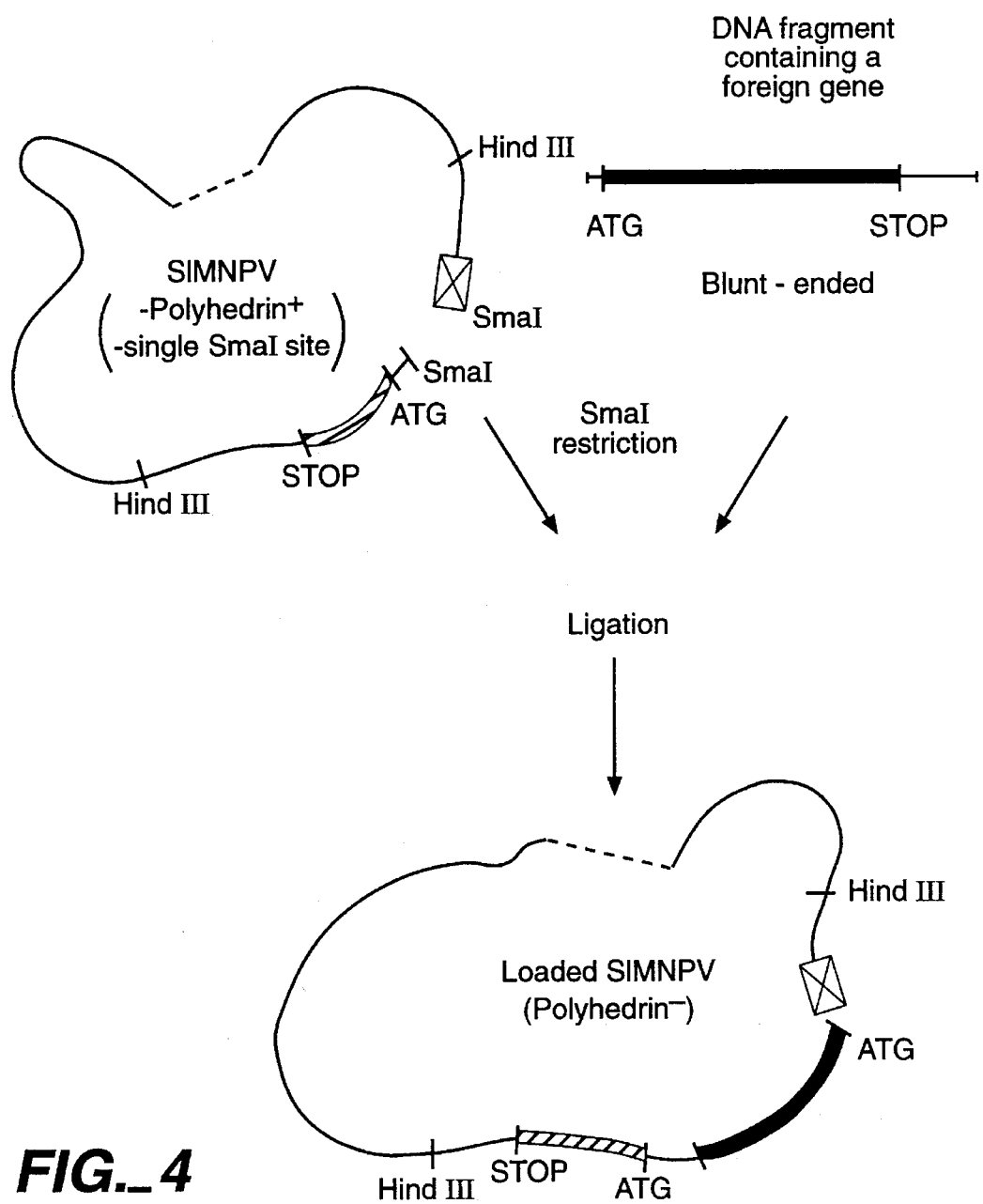
FIG._4

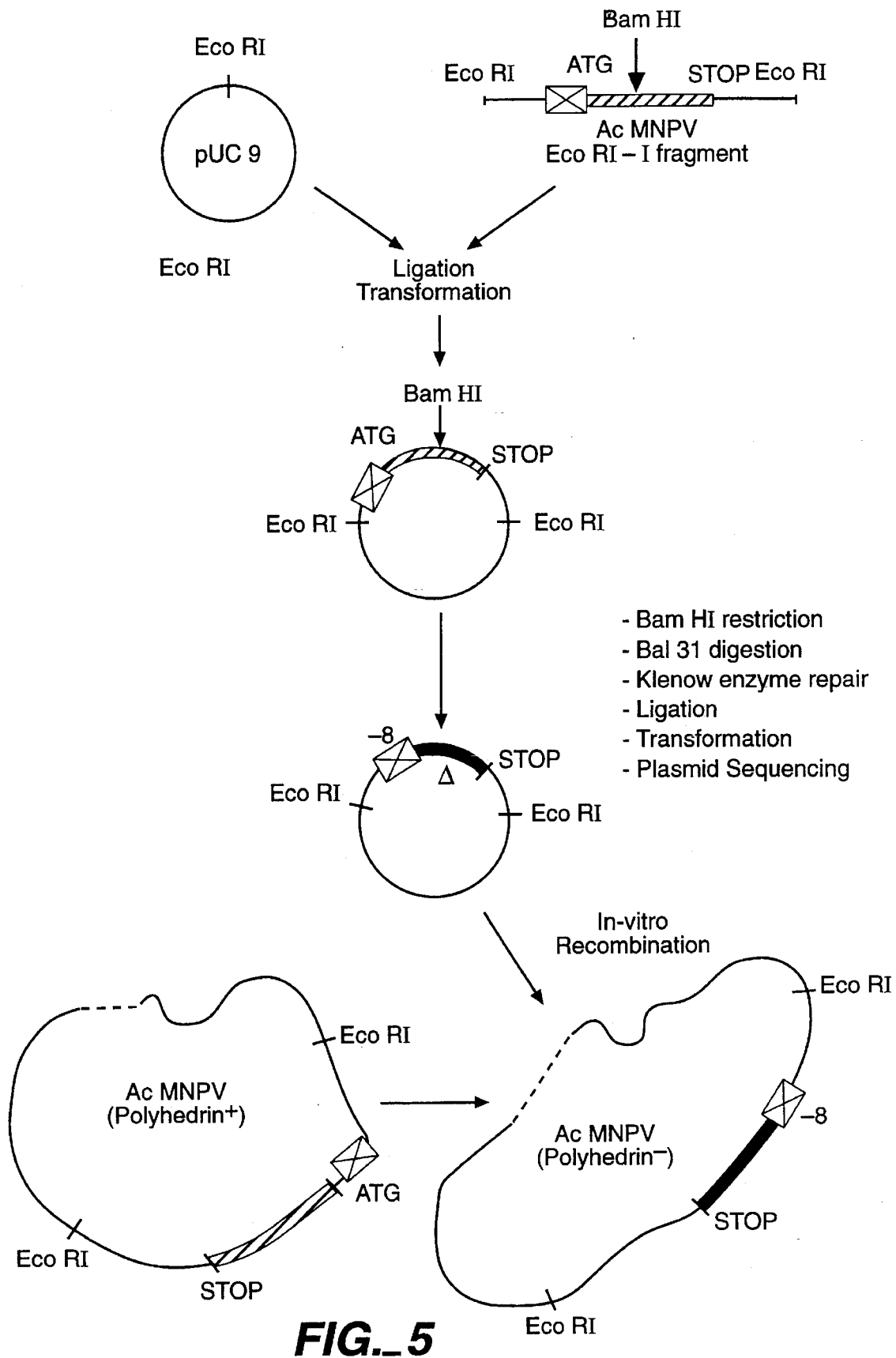
FIG._5

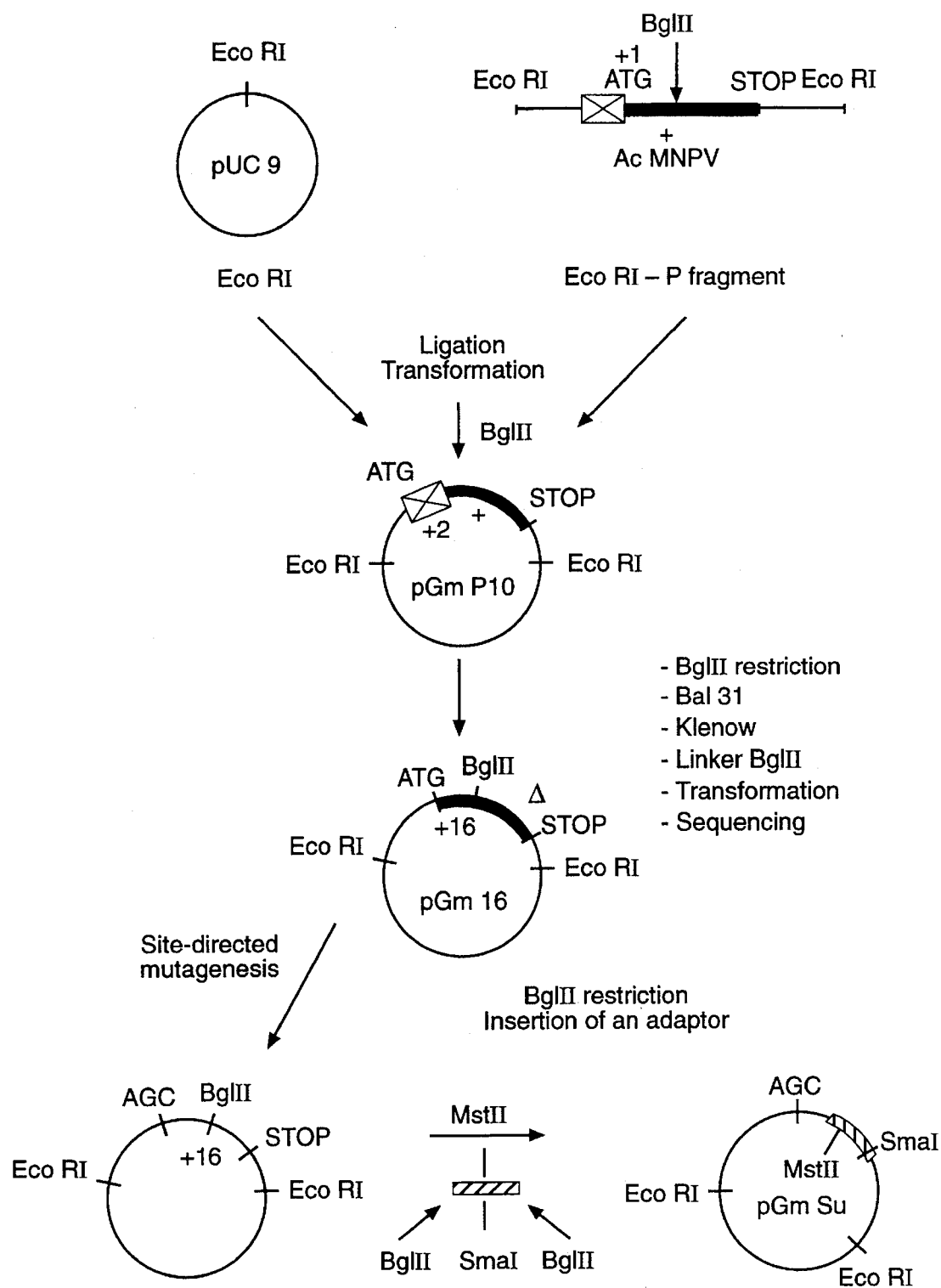
*FIG._6-1*

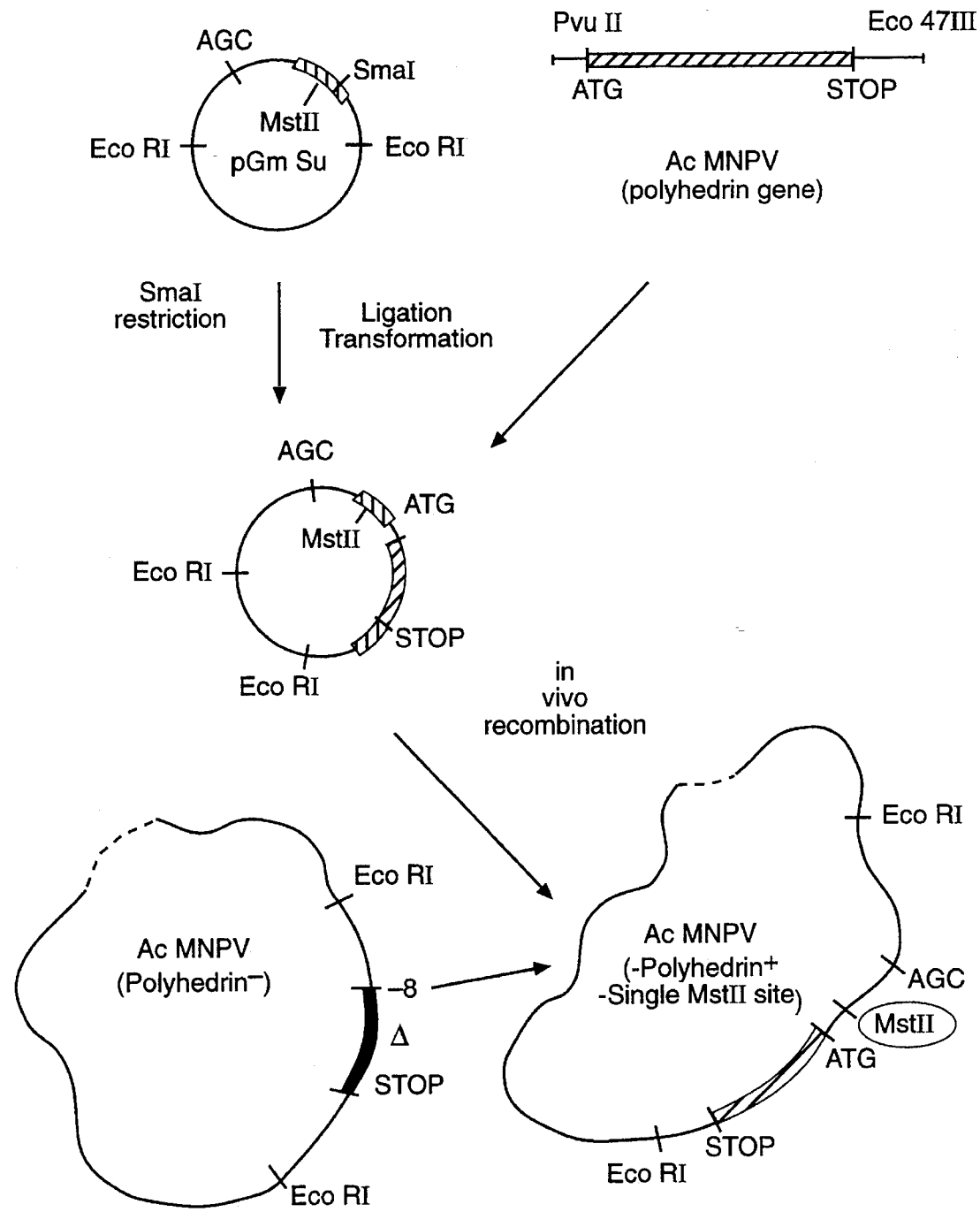
FIG._6-2

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GGGGATCCCG TC            1 2

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

AAATAATAAT AACCGGGCAG GGGGGATCCG                                    30

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CCCGGGGATC CCGTC                                                    15

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: misc_binding
        ( B ) LOCATION: 4..20
        ( D ) OTHER INFORMATION: /note="SEQ ID NO:4 is covalently
            bound between bases 4 and 20 to complementary
            strand, SEQ ID NO:5."

( x i ) SEQUENCE DESCRIPTION: SEQ ID NO:4:

GATCTCCTGA GGTCCCGGGA                                               20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: misc_binding
        ( B ) LOCATION: 5..20
        ( D ) OTHER INFORMATION: /note="SEQ ID NO:5 is covalently
            bound between bases 5 to 20 to complementary
            strand, SEQ ID NO:4."

( x i ) SEQUENCE DESCRIPTION: SEQ ID NO:5:

GATCTCCCGG GACCTCAGGA                                               20

MODIFIED BACULOVIRUS, ITS PREPARATION PROCESS AND ITS APPLICATION AS A GENE EXPRESSION VECTOR

CROSS REFERENCE TO RELATED APPLICATIONS

This is a continuation, of application Ser. No. 07/908,188 filed Jul. 1, 1992, which is a continuation of application Ser. No. 07/358,799, filed May 30, 1989 both abandoned. This is a continuing application of Ser. No. 07/358,799, filed May 30, 1989.

FIELD OF THE INVENTION

This invention relates to a modified baculovirus possessing a unique cleavage site downstream of the promoter of the major polypeptide of the baculovirus viral inclusion, polyhedrin and/or protein P10 genes, to a process for obtaining such a modified baculovirus and to its application as a gene expression vector.

BACKGROUND OF THE INVENTION

Genetic engineering utilizes systems of eukaryotic viral vectors to introduce exogenous DNA into animal or plant cells by transduction. The principal eukaryotic viruses which are likely to serve as DNA transduction vectors in mammalian cells (SV40 and polyoma, for example) and in plant cells (cauliflower mosaic virus, for example) can receive only exogenous ("foreign") DNA of restricted length due to the morphology of the structure of their nucleocapsid. Because the introduction of exogenous DNA could increase the viral genome beyond a size which could be packaged into the viral capsid, it has proved absolutely necessary to have available vectors capable of accepting more exogenous "foreign" DNA, especially since developments in genetic engineering are tending towards attempts to insert more than one foreign gene into a host-cell with the purpose, for example, of obtaining coordinated expression and, if possible, coordinated activity of the products of the foreign genes.

The ideal viral vector must also permit the introduction of lengthy foreign DNA segments into cells at high frequency, with efficient expression of one or more foreign genes.

Virus which seem to fulfill these conditions are the following baculoviruses: nuclear polyhedrosis virus and Autographa californica (AcNPV). L. K. Miller [Chapter 14 in "A Virus Vector for Genetic Engineering in Invertebrates" of the manual "GENETIC ENGINEERING IN PLANT SCIENCES" (1981) N. J. Panopoulos, Ed., Praeger Publ. New-York, pages 203–223] identifies the latter as possessing features potentially useful for use as a vector for the propagation and expression of foreign genes in an eukaryotic environment. See also an earlier article by K. M. Potter and L. K. Miller [ANIMAL VIRUS GENETICS, 6, GENETIC MUTATIONS OF A BACULOVIRUS, ACADEMIC PRESS (1980), pages 71–80].

A number of other publications are also directed to the use of baculovirus systems: European patent application Nos. 0127 839, 0228 036 and 0260 090. These three publications seem to have the common feature of requiring first the creation of a transfer vector, which is a construct capable of accepting a foreign gene, to in effect transfer the foreign gene as a separate step into the virus, a lengthy and delicate process.

An article by Smith, et al., ["PHYSICAL ANALYSIS OF AUTOGRAPHA CALIFORNICA NUCLEAR POLYHEDROSIS VIRUS TRANSCRIPTS FOR POLYHEDRIN AND 10000-MOLECULAR WEIGHT PROTEIN", *Journal of Virology*, (January 1983), pages 215–225] describes the approximate location of the DNA sequences which encode the mRNAs for the polyhedrin and p10 proteins of the AcNPV.

This invention has as its object a modified baculovirus bearing a unique restriction site situated downstream of the ATG codon of a gene encoding for at least one baculovirus-associated protein or downstream of a strong late promoter of the gene for a baculovirus-associated protein, suitable for use in inserting operatively heterologous DNA encoding a desired polypeptide.

This invention also has as it object the process of direct insertion of at least one heterologous DNA sequence into the above-described baculovirus expression vector by in vitro manipulation thus obviating the need for intermediate transfer vectors to achieve said insertion of heterologous DNA.

This invention further has as its object a process for the expression of foreign genes inserted into said baculovirus expression vectors.

SUMMARY OF THE INVENTION

The fundamental predicate of the present invention provides an expression vector based on the baculovirus as such, used to directly infect a host for consequent expression of heterologous DNA contained therein.

The expression vector hereof is tailored to allow the insertion of practically any heterologous DNA sequence without the necessity of a viral or transfer vector intermediate. This reduces the time and number of manipulations necessary to generate the viral expression vector containing the desired heterologous DNA sequences.

This invention additionally provides a process for producing such a modified baculovirus expression vector. The process is characterized in that a suitable restriction site is directly inserted, without recourse to a transfer vector, into the complete or incomplete baculovirus genome downstream of the strong late promoter of the gene for at least one of the proteins which constitute baculovirus-associated formations (whether baculovirus viral occlusions, such as polyhedrin, or baculovirus-associated proteins other than viral occlusions, such as protein P10) in order to obtain a modified virus which constitutes an expression vector configured to have inserted therein operatively heterologous DNA.

In an embodiment for constructing such a modified baculovirus hereof a baculovirus is chosen which lacks restriction sites for at least one given restriction enzyme, and incorporating at least one such unique restriction site at a location suitable for insertion of heterologous DNA operatively under promoter control.

In a preferred embodiment, one employs an original baculovirus lacking a unique restriction site, notably, for example, the nuclear polyhedrosis baculovirus *Spodoptera frugiparda* (Sf).

In a further preferred embodiment, an original baculovirus is engineered to delete a particular restriction site(s).

In the process of producing a modified baculovirus in cases where it is necessary to delete a particular restriction enzyme site(s), the deletion is achieved by co-transfection of DNA from the unmodified baculovirus together with a plasmid comprising a modified viral DNA fragment which spans the restriction site to be deleted. The plasmid containing the viral DNA fragment is modified by digestion with the restriction enzyme specific for the site to be deleted followed by ligation of a linker to the ends of the fragment. The plasmid is then re-circularized and co-transfection with the unmodified baculovirus is then performed to give rise to a recombinant baculovirus which now lacks this restriction enzyme site.

The introduction of a restriction site for a given enzyme downstream of the strong late promoter for at least one of the genes encoding baculovirus-associated formations, and notably the polyhedrin and/or polypeptide P10 genes, is performed by co-transfection of cells with the unmodified baculovirus together with a plasmid into which a fragment containing the restriction site placed downstream of the strong late promoter has been cloned. Said co-transfection leads to the formation of a modified recombined virus which corresponds to an expression vector ready to receive heterologous DNA sequences.

To construct a modified baculovirus which constitutes an expression vector ready to receive at least two foreign DNA fragments, the expression of which is desired, at least two identical or different restriction sites for at least two identical or different enzymes are inserted on a suitably chosen baculovirus.

In the case where the original baculovirus lacks two restriction sites for two identical or different enzymes, these two restriction sites are successively introduced by co-transfection of the unmodified baculovirus together with a first plasmid containing the desired modification of the first restriction site. The resultant recombinant baculovirus is then co-transfected with a second plasmid containing the second desired restriction site. This second co-transfection gives rise to recombinant viruses containing the two desired restriction sites.

In the case where the original baculovirus contains multiple restriction sites at undesirable sites, these sites are deleted by successive co-transfection, as described above, with plasmids lacking each of the restriction sites to be deleted.

In the process for producing a baculovirus expression vector designed to receive heterologous DNA, this vector is characterized by the insertion of a unique restriction site near a gene encoding a baculovirus-associated protein or downstream of the strong late promoter of this gene.

In another process for producing a modified baculovirus constituting an expression vector designed to receive heterologous DNA, this vector is characterized by the presence of two identical or different restriction sites, respectively, inserted near the gene for a baculovirus-associated protein and downstream of the strong late promoter of this gene.

To obtain a modified baculovirus suitable for use as an expression vector, this vector is modified to comprise a unique restriction site inserted downstream of the ATG codon of the gene for at least one baculovirus-associated protein or downstream of a strong late promoter of this gene.

Advantageously in a method for obtaining a modified baculovirus, at least two restriction sites are inserted downstream of the ATG codon of the gene for at least one baculovirus-associated protein and downstream of another strong late promoter of this virus, respectively.

In a preferred embodiment heterologous DNA sequences encoding a desired polypeptide are inserted directly into the above constructed baculovirus expression vectors by in vitro genetic manipulation.

According to one embodiment of said insertion process, at least one heterologous DNA sequence is introduced directly into the modified viral genome that constitutes the initial empty expression vector.

In a presently preferred embodiment, the viral genome is first linearized by the action of a restriction enzyme before the direct insertion of at least one heterologous DNA sequence.

In a preferred embodiment of the said insertion process, a first heterologous DNA fragment is directly inserted into a first restriction site of the said expression vector, then a second heterologous DNA fragment, identical to the first or different from it, is directly introduced into a second restriction site of said expression vector, the two restriction sites being sites for different restriction enzymes.

In a preferred embodiment of said insertion process, the identical or different foreign DNA fragments are inserted into two different restriction sites for one identical enzyme, by partial digestion of said expression vector to create a site into which a first DNA fragment is then introduced, said vector is then subjected to a second partial digestion to create the second site and the second DNA fragment is inserted therein.

According to said insertion process virtually any heterologous DNA sequence may be inserted into said baculovirus expression vectors provided that the sequence preferably does not contain particular restriction sites.

Consequently, the expression vector according to the invention can be used to express any gene coding for prokaryotic and eukaryotic proteins, all sequences coding for biosynthesis genes, viral protein antigens and, in particular, as non-limiting examples, the genes for invertebrate and vertebrate acetylcholinesterases.

BRIEF DESCRIPTION OF THE DRAWINGS

FIG. 1 shows a process of deleting an undesirable SmaI site from a baculovirus.

FIG. 2 shows a process of inserting a SmaI restriction site into a baculovirus.

FIG. 2A shows a process of generating a polyhedrin minus SlMNPV.

FIG. 3 shows creation of SmaI site in the SlMNPV polyhedrin gene.

FIG. 4 shows ligation of a heterologous gene and a modified baculovirus vector and subsequent transfection into cells.

FIG. 5 shows deletion of the polyhedrin gene from an AcMNPV virus.

FIG. 6 (parts 1 and 2) show insertion of a MstII site into a modified AcMNPV vector.

The following examples are offered by way of illustration and not by way of limitation.

DETAILED DESCRIPTION OF THE INVENTION

EXAMPLES

Example 1: Deletion of the SmaI of the SlMNPV Genome

To construct the baculovirus expression vector, i.e., the modified baculovirus ready to receive foreign DNA sequences, a baculovirus lacking a restriction site for a given enzyme is selected; this is exceptional but is the case with the baculovirus of nuclear polyhedrosis of *Spodoptera frugiperda*, which does not contain a SmaI restriction site.

One or more undesirable restriction sites can be deleted from the baculovirus genome: the single SmaI site located in the Pst-I-G fragment of the baculovirus of nuclear polyhedrosis of *Spodoptera littoralis* is notably deleted by the following process:

The Pst-I-G fragment of SlMNPV cloned into a plasmid of the pAT153 type is cleaved with SmaI and a KpnI linker is ligated to the linearized plasmid. The resulting plasmid is devoid of the SmaI site and is co-transfected with the original SlMNPV in order to obtain recombinant viruses lacking the SmaI site. Recombinant viruses are selected from the descendants of the viruses obtained after co-transfection. Compared with the original virus, these viruses will have lost an SmaI site, i.e., will no longer have the SmaI site but will have acquired a KpnI site and thus will possess a total of 7+1=8 KpnI sites. The following procedure is used to select these recombinant viruses: polyhedra harvested after death of transfected caterpillars are used as the source of DNA for a new transfection. Before this new transfection, the DNA is cleaved with SmaI. This treatment has the effect of eliminating the multiplication of unmodified viruses since their genome is cleaved, therefore, only the multiplication of recombinant viruses occurs. Several cycles of virus multiplication on this basis may be needed to eliminate the descendants of the original viruses which initially escaped cleavage by SmaI.

This process of deleting an undesirable SmaI restriction site is illustrated in FIG. 1.

Example 2: Insertion of an SmaI Site Downstream of the Polyhedrin Promoter on a Baculovirus Devoid of an SmaI Restriction Site The unique site, whether SmaI or any other, must be placed near the ATG (initiation) codon of the gene for polyhedrin (or P10). When this site is placed before the ATG codon, it allows expression of the foreign gene under the control of its own ATG (the position of the site of insertion is said to be upstream of the ATG, i.e., on the 5' side of the ATG). This is the most commonly desired situation. When the novel restriction site is placed downstream of the ATG (i.e., on the 3' side of this ATG), this allows the production of so-called fused proteins which, under control of the polyhedrin ATG, comprise amino acids corresponding to the fused polyhedrin sequence in the N-terminal part and amino acids corresponding to the fused foreign sequence in the C-terminal part. The region in which the site is inserted may, as an illustration only, extend from −10n to +10n. (It is conventional to number the A of ATG as +1, the T as +2 and the G as +3; bases before ATG are numbered with minus signs (−); the base which precedes A is numbered −1, and so forth).

The choice of SmaI is governed by the relative rarity of SmaI sites in baculovirus. The fact that the viral DNA is cleaved at this endonuclease SmaI recognition site with the production of blunt ends is certainly an advantage since the blunt ends constitute a universal entrance for foreign sequences. This advantage is not determinant in the choice of restriction sites since it is common practice to blunt those ends generated by enzymes which not create blunt ends. Any restriction endonuclease able to recognize a unique restriction site located suitably downstream of a promoter allows the introduction of foreign sequences for the expression of inserted genes, sometimes at the price of minor modifications of their termini.

In accordance with the invention, on a virus lacking an SmaI restriction site, for example, either NPV of *Spodoptera frugiperda* or of *Spodoptera littoralis* treated according to Example 1, it is necessary to insert an SmaI site (which becomes a unique site in the modified viral genome) downstream of the polyhedrin gene promoter (or of any other strong late promoter such as that of protein P10). The insertion of the SmaI site at the best location pre-supposes that the polyhedrin gene sequence is first established (notably the promoter region).

To insert the SmaI site, it is necessary to have available a unique restriction site which allows the genome to be opened in a restricted part of the polyhedrin gene. Unique sites are rare in the whole virus. The probability of finding a unique site increases when the sequence size is reduced.

This introduction may be undertaken by several methods. These include, directed mutation to create unique sites, followed by introduction of a SmaI linker into these sites.

Another method is to create Ba131, -induced deletions following cleavage of the viral sequence at the SacI site. Since there is a second SacI site in the plasmid polylinker, it is necessary to delete this SacI site from the polylinker prior to digestion with Ba131.

The polylinker initially has the following composition: EcoRI; SacI; KpnI; SmaI; BamHI; XbaI; SalI; PstI; SphI; HindIII.

After cloning the HindIII fragment in pUC19, directional deletions are undertaken with the ExoIII-Mung bean system. The blockage site is the PstI site contained in the polylinker 5' region, and the digestion site is a HpaI site located between the polylinker and the XbaI site of the HindIII-K fragment. This deletion leads to the disappearance of a segment comprised between PstI and HpaI on the one hand and of a segment comprised between the same HpaI site and the viral XbaI site on the other hand.

The deleted plasmid is prepared for direct sequencing (simply for reasons of commodity) of plasmids later deleted around the XbaI site of the viral sequence. At this stage, the polylinker has the following composition: EcoRI; SacI; KpnI; SmaI; BamHI; XbaI; SalI and the first significant viral site at the 3' end of the polylinker is XbaI.

The SacI site of the polylinker is then eliminated by double EcoRI-BamHI digestion, which leaves the polylinker with only the XbaI and SalI sites. In this way, it is possible both to delete around the SacI site and to insert in place of this deletion a SmaI linker which will be a unique site in this plasmid. The position of the SmaI site must be from −30 to +10 since XbaI is in position −40 relative to the A of ATG.

Plasmids p13.21XSS are co-transfected on *S. littoralis* cell cultures and the recombined viruses corresponding to the expression vector lacking inserted heterologous DNA sequences are detected by the "P minus" phenotype. This phenotype is that of the viruses responsible for infectious foci in which polyhedra cannot be detected in the plaque lysis method.

This process for inserting a SmaI restriction site is illustrated in FIG. 2.

Example 3: Inserting a Foreign Sequence Immediately Upstream of the ATG Codon

This step in the construction of the expression vector pre-supposes the possession of baculovirus modified in accordance with the invention, i.e., virus with a unique site located, for example, at −4 (the numbering reference always being +1 for the A of the initial ATG of the polyhedrin gene). The said modified virus contains a deletion of nucleotides −3 to about +280, relative to unmodified virus, since the SacI site from which Ba131 digestion begins is located at +140. The preparation of the vector assumes the preparation of a foreign sequence able to be expressed.

Sequence Inserted: the Acetylcholinesterase Sequence of *Drosophila melanogaster.*

The sequence to be expressed is obtained from the replicative form of plasmid pEMBL-Ache for *D. melanogaster* acetylcholinesterase (plasmid pE6 obtained by Fournier et al., INRA, Antibes). The sequence originally published by Hall and Spierer (EMBO J., 1986, page 2952) is 3481 bases long. The NruI-SacI segment which extends from +869 to +3481 can be usefully subcloned in pUC19 to SmaI-SacI. NruI cleaves the acetylcholinesterase gene 127 bases upstream of the ATG of this gene. A unique AatII site at +921 allows recovery of the AatII-SacI fragment which includes the entire Ache gene (i.e., a leader sequence of 72 bases, an ORF of 1947 bases and a 3' sequence of 241 bases that includes a polyadenylation signal at +3050).

In order to avoid the presence of the sequence coding for the anchoring tail and to make purification of the acetylcholinesterase easier, it is beneficial to use the AatII-XmnI segment (+921 to +2856), which gives a truncated protein of 28 out of 649 amino acids downstream of the Drosophila Ache gene. The result of this assembly leads to a protein fused at 3'. The nature of the fused protein depends on the residues obtained by the Bal31-induced deletion. After the AGTGGG sequence formed by the last codon of Ache and the GGG codon, which is an SmaI half-site, there follows either the bases of the polyhedrin gene in the proper reading frame, in which case the fused protein contains about 120 amino acids of polyhedrin, or bases which are out of frame with stop codons which appear after about 30 sense codons.

The ends of the double-stranded DNA fragment to be inserted into the modified virus at the SmaI site are made blunt, if necessary, by the action of Mung-bean nuclease for sites SacI and AatII.

After transfection of *Spodoptera littoralis* cells, the acetylcholinesterase activity is measured in a series of supernatants and/or homogenates derived from cells isolated 48 hours after infection and maintained for an additional 48 hours to produce acetylcholinesterase. Batches with high enzyme action are cloned by limit dilution. The presence of positive clones is confirmed by hybridization with a pUC-Ache probe.

Example 4: Insertion of Heterologous Sequences Downstream of the ATG (to generate fused proteins) Expression of the beta-galactosidase Gene Like the preceding example, this one assumes the existence of modified baculovirus. In this case, the deletion produced by Bal31 from the SacI site spares the ATG. The SmaI-SalI fragment of Casadaban plasmid pMC1871 (plasmid distributed by Pharmacia) is inserted into the SmaI site of the transformed virus after modification of the SalI termini by Mung-bean nuclease.

This Construction Shows the Following Structure:

←polyhedrin promoter - ATG TAT - ←GGG GAT CCC GTC - LacZ -
AAA TAA TAA TAA CCG GGC AGG GGG GAT CCG→ - 3' terminal of polyhedrin ORF
(polyhedrin promoter - ATG TAT - ←- SEQ ID NO: 1 - LacZ -
SEQ ID NO: 2 → - 3' terminal of polyhedrin ORF)

Recombined viruses with this structure are recognized in cell culture by their blue staining with X-gal.

Example 5: Installation of a Unique SmaI Site Downstream of the Polyhedrin Promoter In conformity with the invention, in a virus lacking an SmaI restriction site, for example either the MNPV of *Spodoptera frugiperda*, or the MNPV of *Spodoptera littoralis* treated according to Example 1, a SmaI site (which become a unique site in the modified virus) should be inserted downstream of the promoter of the polyhedrin gene. The insertion of the SmaI site at the best place implies the prior establishment of the sequence of the polyhedrin gene (especially the promoter region).

Preferred methods of carrying out this introduction are exemplified below.

1. Insertion of a SmaI linker in the *Spodoptera littoralis* MNPV polyhedrin gene A. Production of a virus no longer expressing polyhedrin.

According to this method, the viral sequence is cleaved at the SacI site in the structural gene of polyhedrin, and Bal31-induced deletions are performed in order to delete at least part of this structural gene; the modified virus obtained may be used as a starting material for the insertion of a SmaI restriction site.

To obtain said virus, the HindIII-K fragment containing the polyhedrin gene is cloned into the HindIII site of the polylinker of the plasmid pUC19. The orientation of the polyhedrin gene inside the plasmid is then determined.

The polylinker of pUC19 initially has the following restriction sites: EcoRI, SacI, KpnI, SmaI, BamHI, SbaI, SalI, PStI, SphI, HindIII. Since there is a SmaI site in the polylinker of pUC19, it is necessary to delete this SacI site from the polylinker prior to digestion with SacI and Bal31.

After cloning the HindIII fragment in pUC19, directional deletion is undertaken with the ExoIII-Mung bean nuclease system. The blockage site is the PstI site contained in the polylinker 5' region, and the digestion site is an HpaI site located between the polylinker and the XbaI site of the HindIII-K fragment. This deletion leads to the disappearance of a segment comprised between PstI and HpaI on the one hand and of a segment comprised between the same HpaI site and the viral XbaI site on the other hand.

The deleted plasmid is prepared for direct sequencing (simply for reasons of commodity) of plasmids later deleted around the XbaI site of the viral sequence. At this stage, the polylinker has the following composition: EcoRI, SacI, KpnI, smaI, BamHI, XbaI, SalI, and the first significant viral site at the 3' end is XbaI.

The SacI site of the polylinker is then eliminated by double EcoRI-BamHI digestion, which leaves the polylinker with only the XbaI and SalI sites.

Bi-directional deletions were then carried out from the SacI site in the polyhedrin structural gene, using Bal31 exonuclease so as to eliminate at least part of the polyhedrin structural gene. Plasmid pUC9 may also be used in place of pUC19: in this case, since the polylinker of pUC9 lacks a SacI site, the step in which this site is deleted is eliminated; this process is illustrated in FIGS. 2 and 2a.

After repairing the ends with Klenow polymerase, the plasmid is then circularized. The plasmids obtained after bacterial transformation are assessed by sequencing and then recombined in vivo by cotransfection of *S. littoralis* cell cultures with purified DNA from the baculovirus S1MNPV.

The viruses exhibiting a polyhedrin negative phenotype are selected, purified and then amplified.

B. Insertion of a SmaI site.

It is possible to insert, in place of the deletion around the SacI site, a SmaI linker which will be a unique SmaI site in the resulting plasmid. The position of the SmaI site must be from −30 to +10, since XbaI is in position −40 relative to the A of ATG.

The resulting plasmid, named p13.21X88 is co-transfected with DNA of wild type SlMNPV baculoviruses on *S. littoralis* cell cultures. The recombined viruses having an unique SmaI site under control of the polyhedrin promoter, and lacking at least part of the polyhedrin gene, exhibit a polyhedrin negative phenotype. These virus are selected, purified and then amplified.

The resulting plasmids correspond to expression vectors lacking heterologous DNA sequences.

2. Creation of a SmaI Site in the *Spodoptera littoralis* MNPV Polyhedrin Gene (FIG. 3)

From the HindIII-K fragment cloned into the vector pUC, a cleavage site for the SmaI restriction endonuclease was created by site-directed mutagenesis downstream of the sequence of the polyhedrin promoter. The plasmid was then recombined in vivo with the DNA of the virus *Spodoptera littoralis* MNPV modified as described above, (Example 5, 1-A), and no longer expresses polyhedrin.

The viruses exhibiting a polyhedrin positive phenotype are selected, purified and then amplified. The presence of the SmaI site in genomic DNA of the virus is verified by restriction endonuclease cleavage.

The ends of the double-stranded DNA fragment to be inserted into the modified virus at the SmaI site are made blunt, if necessary, by the action of Mung-bean nuclease for sites SacI and AatIII.

After transfection of *Spodoptera littoralis* cells, the acetylcholinesterase activity is measured in a series of supernatants and/or homogenates derived from cells isolated 48 hours after transfection and maintained for an additional 48 hours to produce acetylcholinesterase. Batches with high enzyme activity are cloned by limit dilution. The presence of positive clones is confirmed by hybridization with a pUC-Ache probe.

2) Sequence Inserted: The Lacz Sequence from Plasmid pMC1871

The baculovirus *Spodoptera littoralis* MNPV is modified at the polyhedrin locus, according to Example 5-2.

The SmaI-saII fragment of the plasmid pMC1871 [Shapira, S. K. et al. Gene 25, 71, 1983 (distributed by PHARMACIA)] is purified and then ligated into the SmaI site of the virus so as to preserve the reading frame and thereby to obtain a fusion protein.

This Construct has the Following Structure:

Polyhedrin promoter - ATG TAT - CCC GGG GAT CCC GTC -
LacZ - AAA TAA TAA TAA CCG GGC AGG GGG GAT CCG - 3' end of polyhedrin.
(Polyedrin promoter - ATG TAT - SEQ ID NO: 3 -LacZ -
SEQ ID NO: 2 - 3' end of polyhedrin)

The resulting viruses correspond to expression vectors void of heterologous DNA sequences.

Example 6: Cloning of Heterologous DNA Sequences into the Virus

Ten μg of purified DNA of a virus obtained as described in Example 5 are digested with SmaI endonuclease. The DNA fragment containing the heterologous gene is then added directly to the viral DNA. The ligation is carried out for 24 hours at 16° C. The ligation product is used directly for the transfection of *Spodoptera littoralis* cells (FIG. 4).

1) Sequence inserted: the Acetylcholinesterase Sequence of *Drosophila melanogaster*

The sequence to be expressed is obtained from the replicative form of plasmid pEMBL-Ache for *D. melanogaster acetylcholinesterase* (plasmid pE6 obtained by Fournier et al., INRA, Antibes). The sequence originally published by Hall and Spierer (EMBO J., 1986, page 2952) is 3481 bases long. The NruI segment which extends from +869 to +3481 can be usefully subcloned in pUC19 to SmaI-SmaI. NrUI cleaves the acetylcholinesterase gene 127 bases upstream of the ATG of this gene. A unique AatII site at+921 allows recovery of the AatII-AacI fragment which includes the entire Ache gene (i.e. a leader sequence of 72 bases, an ORF of 1947 bases and a 3' sequence of 241 bases that includes a polyadenylation signal at +3050).

In order to avoid the presence of the sequence coding for the anchoring tail, and in order to make purification of the acetylcholinesterase easier, it is beneficial to use the AatII-XmnI segment (+921 to +2856), which gives a truncated protein of 28 out of 649 amino acids downstream of the Drosophila Ache gene. The result of this construction leads to a protein fused at the 3' terminus. The nature of the fused protein depends on the residues obtained by the Bal31-induced deletion. After the AGTGGG sequence formed by the last codon of Ache and the GGG codon, which is an SmaI half-site, there then follows either the bases of the polyhedrin gene in the proper reading frame, in which case the fused protein contains about 120 amino acids of polyhedrin, or bases which are out of frame with a stop codon which appears after about 30 in-frame codons.

The *Spodoptera littoralis* cells are directly transfected with the ligation mixture.

The expression of recombinant viruses may be directly visualized in cell cultures by simply adding the enzyme substrate (X-Gal) into the medium used for carrying out the plaque lysis assay. The plaques containing a recombinant virus then take on a intense blue color.

The recombinant viruses also exhibit a polyhedrin negative phenotype.

Example 7: Insertion of a Unique Restriction Site (MstII site) Downstream of the P10 Protein Promoter of the Baculovirus *Autographa californica* MNPV The genome of the baculovirus of *Autographa californica* naturally lacks a MstII site. A MstII site was introduced downstream of the P10 protein promoter by homologous recombination in vivo. To facilitate the selection of the recombinant Viruses, polyhedrin was used as a marker. For this, the polyhedrin gene was deleted from a virus (AcMNPV) and a virus no longer producing polyhedra was thus obtained. The polyhedrin gene was then reinserted downstream of the P10 protein promoter.

A. Deletion of the Polyhedrin Gene from an AcMNPV Virus (FIG. 5)

The procedure is similar to the one described above for the virus *Spodoptera littoralis* MNPV.

The EcoRI-I fragment containing the polyhedrin gene of the AcMNPV virus was cloned into a pUC9 vector at the EcoRI site of the polylinker. The polyhedrin gene was deleted by digestion with the endonuclease Bal31. After repairing the ends using Klenow polymerase, the plasmid was self-ligated. The plasmids obtained after transformation of bacteria were sequenced in order to verify the extent of deletion of the polyhedrin gene.

Deletion of the polyhedrin gene from the genome of the wild virus was obtained by homologous recombination between a plasmid containing a total deletion of the polyhedrin gene, and purified DNA of the AcMNPV virus.

The viruses exhibiting a polyhedrin negative phenotype were selected, purified and then amplified.

B. Insertion of an MstII Site into the P10 Vector (FIGS. 6-1 and 6-2) The EcoRI-P fragment containing the P10 protein gene of the AcMNPV virus was cloned into a pUC9 vector at the EcoRI site of the polylinker. The P10 protein gene was then digested with exonuclease Bal31. After repairing the ends with Klenow polymerase, BglII linkers were ligated to the ends and the plasmid was self-ligated. The plasmids recovered from transformed bacteria were sequenced. Among the plasmids of interest, some plasmids, which have lost the P10 protein ATG, will permit expression of foreign genes possessing their own initiator ATG. Others still possessing the P10 ATG will give fusion proteins.

One of the resulting plasmids, named pGm16, possessing a BglII site at +16 (from the A of the ATG of P10), forms the basis of the following constructs. Several modifications have been made to this plasmid:

1. Mutation of ATG to AGG.
2. Insertion of the following adaptor, SEQ ID NO: 4 and SEQ ID NO: 5, into the
   BglII site:
   5' GATCT CCTGAGGT CCCGGG A 3'
   3'      A GGA CTTCCA GGGCCC TCTAG 5'
   BglII MstII SmaI BglII
   The new vector obtained is called pGmSU.

3. Insertion of the polyhedrin gene into the SmaI site of the vector pGmSU.

The plasmid pAcI containing the polyhedrin gene is digested with the endonucleases PvuII and Eco47III thus releasing the complete polyhedrin gene from AcMNPV. After purification, the fragment is ligated with the vector pGmSU which is linearized with the endonuclease SmaI. The plasmids obtained after transformation of the bacteria with the ligation mixture were selected for the presence of the polyhedrin gene in the proper orientation.

4. The plasmid thus obtained was recombined in vivo with purified DNA of the baculovirus AcMNPV, modified as described in Example 6A above, that is to say no longer producing polyhedrin. The viruses exhibiting a polyhedrin positive phenotype were purified and then amplified. The presence of the MstII site in the genomic DNA of the virus was verified.

Example 8: Insertion of a Foreign Sequence Downstream of the P10 Promoter

This stage in the construction of the expression vector presupposes the possession of a baculovirus modified according to Example 7, that is, a virus possessing a unique site situated, for example at +16 in the P10 locus (the reference for numbering always being +1 for the A of the initiator ATG of the P10 protein). Sequence inserted: acetylcholinesterase (Ache) sequence from the head of *Drosophila melanogaster*. The ends generated by FsppI and SacI digestion (the end generated by the endonuclease SacI which is not blunt, must be repaired by the DNA polymerase of the phage T4) permit the production of a fragment containing the complete Ache gene, from its initiator ATG to its stop codon.

Ligation

The purified DNA of a modified virus obtained according to Example 7, is digested with the endonuclease MstII. The ends are repaired using the Klenow enzyme. Ten μg of linearized viral DNA are ligated with an excess of purified FspI-SacI fragment (blunt-ended) of pEMBL-Ache containing the complete Ache gene. The incubation is carried out for 24 hours at 16° C. The ligation mixture is used directly for transfecting the *Spodoptera frugiperda* Sf9 cells.

Five days after transfection, the recombinant viruses are selected by the plaque lysis technique. The viruses no longer producing polyhedra are selected, purified and then amplified.

The expression of the foreign protein is then analyzed in extracts derived from cells infected with the recombinant viruses.

All publications mentioned in this specification are indicative of the level of skill of those skilled in the art to which this invention pertains. All publications are herein incorporated by reference to the same extent as if each individual publication was specifically and individually indicated to be incorporated by reference.

The invention now being fully described, it will be apparent to one of ordinary skill in the art that many changes and modifications can be made thereto without departing from the spirit or scope of the appended claims.

---

What is claimed is:

1. A process for preparing a modified baculovirus genome comprising:

inserting operatively a restriction site for SmaI into the DNA of SIMNPV wherein a SmaI site has previously been deleted, said inserted SmaI site being under control of the promoter of the polyhedrin gene; or inserting operatively a restriction site for SmaI into the DNA of SIMNPV, said inserted SmaI site being under control of the promoter of the polyhedrin gene; or inserting operatively a restriction site for MstII into the DNA of AcMNPV, said inserted MstII site being under control of the promoter of the P10 gene.

2. The process according to claim 1 wherein the SmaI site is inserted at a position localized between about −30 and +10, relative to the A(+1) of ATG of the polyhedrin sequence.

3. The process according to claim 2 wherein a part of the polyhedrin gene is deleted before insertion of the restriction site.

4. A process for preparing a SIMNPV baculovirus genome devoid of Sma I sites comprising:

(a) inserting a fragment of SIMNPV baculovirus DNA comprising a site for Sma I into a plasmid devoid of any such site,
(b) cleaving the plasmid of step (a) with Sma I,
(c) ligating a DNA fragment devoid of any site for Sma I and comprising a Kpn I linker at the site of said cleaving,
(d) cotransfecting the recombinant vector of step (c) with SIMNPV baculovirus DNA in a suitable host,
(e) treating the DNA of baculovirus recovered from the host cells with Sma I, and
(f) collecting non-cleaved DNA fragments.

5. The process according to claim 4 comprising a step g) wherein the DNA fragments of step f) are used for transfecting suitable host cells and wherein steps e), f) and g) are performed a plurality of times.

* * * * *